United States Patent [19]
Doutre et al.

[11] Patent Number: 5,827,982
[45] Date of Patent: Oct. 27, 1998

[54] PORTABLE LIQUID METAL FILTRATION DEVICE FOR INCLUSION ANALYSIS

[75] Inventors: Don Allen Doutre, Kingston; Gary Hay, Ontario; Peter Alexander Wales, Kingston, all of Canada

[73] Assignee: Alcan International Limited, Montreal, Canada

[21] Appl. No.: 810,152

[22] Filed: Feb. 25, 1997

[51] Int. Cl.$^6$ .............................. G01N 1/00; G01N 11/00; C21B 3/04

[52] U.S. Cl. ..................... 73/863.23; 73/61.73; 266/227

[58] Field of Search ................. 73/19.01, 61.73, 73/61.74, 61.76, 863.31, 863.23; 266/227, 238, 239; 75/412, 407, 408, 409, 410, 411; 164/134; 210/808, 406, 500.1, 510.1

[56] References Cited

U.S. PATENT DOCUMENTS

| | | | |
|---|---|---|---|
| 3,661,373 | 5/1972 | Cheltsov et al. . | |
| 3,893,917 | 7/1975 | Pryor et al. | 210/69 |
| 4,039,322 | 8/1977 | DiMartini et al. | 75/63 |
| 4,081,371 | 3/1978 | Yarwood et al. | 210/69 |
| 4,366,721 | 1/1983 | Pelton . | |
| 4,964,993 | 10/1990 | Stankiewicz | 210/510.1 |
| 5,139,238 | 8/1992 | Buhr | 266/238 |
| 5,370,171 | 12/1994 | Fields et al. | 164/312 |

FOREIGN PATENT DOCUMENTS

| | | |
|---|---|---|
| 2019205 | 6/1990 | Canada . |
| 59-202063 | 11/1984 | Japan . |
| 60-005829 | 1/1985 | Japan . |
| 61-159132 | 7/1986 | Japan . |
| 61-243133 | 10/1986 | Japan . |
| 4-005567 | 1/1992 | Japan . |
| 6-042885 | 2/1994 | Japan . |
| WO 96/23222 | 8/1996 | WIPO . |
| WO9718339 | 5/1997 | WIPO . |
| WO9718456 | 5/1997 | WIPO . |

OTHER PUBLICATIONS

Michael J. Lessiter, Editor. Wayne M. Rasmussen, AFS/CMI "To Pour or Not to Pour the Dilemma of Assessing Your Aluminum Melt's Cleanliness", Modern Casting, Feb. 1996, pp. 45–48.

W.J. Beek and K.M.K. Muttzall "Transport Phenomena", 1975, John Wiley & Sons Ltd., pp. 156–160.

"B-3 Refractory Board for Precision Machined Shapes", Pyrotek. Two pages.

"Pyrotek Vacuum Formed Products Manufactured to Meet Customer's Specifications", Pyrotek. One page.

Primary Examiner—Michael Brock
Assistant Examiner—Jay L. Politzer
Attorney, Agent, or Firm—Cooper & Dunham LLP

[57] ABSTRACT

A device for measuring metal purity, comprising a receptacle for holding a sample of molten metal, the receptacle being made, at least internally, from an insulating refractory material and having a bottom wall provided with a hole containing a filter element. The bottom wall is substantially impermeable to air except at the hold. An enclosed collection vessel is positioned below the receptacle for collecting molten metal which passes through the filter element from the receptacle, the collection vessel having an opening permitting extraction of gas from within the vessel to enable a vacuum to be generated within the vessel during use of the device. A leak-tight seal is established between the receptacle for molten metal and the collection vessel to permit vacuum generated in the collection vessel to draw molten metal into the collection vessel from the receptacle through the filter. The receptacle for molten metal has a heat diffusivity value that is sufficiently low that, in use, the temperature of the molten metal in the receptacle does not fall below the liquidus temperature in a period of time required for the vacuum to draw a fixed amount of molten metal sufficient for metal purity testing purposes through the filter and into the collection vessel from the receptacle. The invention also relates to a corresponding method, and to novel parts of the device.

36 Claims, 2 Drawing Sheets

PORTABLE LIQUID METAL FILTRATION DEVICE FOR INCLUSION ANALYSIS

BACKGROUND OF THE INVENTION

I. Field of the Invention

This invention relates to an apparatus and method for measuring the number and/or type of inclusions in a molten metal. More particularly, the invention relates to an apparatus and method of this kind which can be employed in metal casting plants and foundries.

II. Description of the Prior Art

The measurement of the number and type of inclusions in molten metal is a necessary quality control technique in most casting plants. Inclusions in metal may adversely affect many of the performance requirements of the metal products resulting from such casting and a reliable means of making such measurements is an essential part of quality control.

A method frequency used to perform such measurements involves collecting the solid material from a known quantity of molten metal on a filter element, then examining the filter element to determine the number of inclusions in the molten metal sample, and also (if required) the type.

Japan Laid-Open application JP 59-202603 (assigned to Nippon Light Metal) discloses one such apparatus consisting of a heated receptacle with a filter, and a collection vessel below the filter with a load cell to measure the weight of metal therein. The heated receptacle is placed within a pressure vessel. In use, a quantity of molten metal is placed within the heated receptacle, a cover is mounted in place and pressurized. Metal is forced through the filter and collects in the collection vessel. The load cell is used to weigh the metal collected and determine the amount of metal which passes through the filter. When a fixed amount of metal has passed through the filter, the pressure is released, the sample frozen and examined to measure the quantity of material collected.

Such devices are useful in large casting operations where they can be used in a fixed test location, for example along a metal conveying trough, but because of the requirements of the heaters and load cells, the devices lack portability and ease of use.

There is a need for a metal sampling device which permits a similar quantitative measurement of inclusion numbers and types, but has a high degree of portability making it suitable for a wide range of foundry operations, including, for example, shape casting foundries.

SUMMARY OF THE INVENTION

An object of the present invention is to provide a compact and portable apparatus for quantitative and/or qualitative measurement of inclusions in molten metal, which does not require the use of heater circuits or balances and load cells.

Another object is to provide a method of measuring inclusions in molten metal which does not require heaters or balances and load cells.

Another object is to provide an apparatus and method for quantitative and/or qualitative measurement of inclusions in molten metal which is highly portable and preferably does not require any electrical power to operate.

Yet another object of the invention, at least in its preferred forms, is to provide an apparatus and method for quantitative and/or qualitative measurement of inclusions in molten metal that can avoid the need to generate above-atmospheric pressures in the apparatus, and therefore avoid the need for pressure enclosures around a vessel used for receiving the molten metal to be tested.

According to one aspect of the invention, there is provided a device for measuring metal purity, comprising: a receptacle for holding a sample of molten metal having a liquidus temperature, said receptacle being made, at least internally, from an insulating refractory material having a heat diffusivity value, said receptacle having a bottom wall provided with a hold, and said bottom wall being substantially impermeable to air except at said hole; a filter element for collecting impurities from said molten metal, said filter element being positioned in said hole; and an enclosed collection vessel positioned below said receptacle for collecting molten metal which passes through the filter element from said receptacle, said collection vessel having an opening permitting extraction of gas from within said vessel to enable a vacuum to be generated within said vessel during use of the device; wherein a leak-tight seal is established between said receptacle for molten metal and said collection vessel to permit vacuum generated in said collection vessel to draw molten metal into said collection vessel from said receptacle through aid filter; and wherein said heat diffusivity value is sufficiently low that, in use, the temperature of the molten metal in said receptacle does not fall below the liquidus temperature in a period of time required for said vacuum to draw a fixed amount of said molten metal sufficient for metal purity testing purposes from said receptacle through said filter and into said collection vessel.

The term "heat diffusivity" is used herein to define the combination of material properties in certain differential equations governing heat flow into bodies and has units of joules.m$^{-2}$.°C.$^{-1}$.seconds$^{-\frac{1}{2}}$. It is used, for example, in heat flow equations describing heat penetration into semi-infinite media, as described in Transport Phenomena, by W. J. Beek and K. M. K. Muttzall, Wiley-Interscience (1975) pages 157 to 160.

The heat diffusivity of a material is defined by the equation:

$$\text{Heat diffusivity} = \sqrt{K \times \rho \times C_p}$$

wherein:

K is the thermal conductivity of the material in watt/m/°C.;

$\rho$ is the density in kg/m$^3$; and $C_p$ is the heat capacity of the material in joules/°C./kg.

In the present invention, K should preferably be less than about 0.5 watt/m/°C.; $\rho$ should preferably be less than 1000 kg/m$^3$; and $C_p$ should preferably be less than 1000 to 1200 joules/°C./kg. The heat diffusivity (taking the three properties into account) should preferably be less than 500 joules.m$^{-2}$.°C$^{-1}$.seconds$^{-\frac{1}{2}}$, and more preferably less than 350 joules.m$^{-2}$.°C.$^{-1}$.seconds$^{-\frac{1}{2}}$, and more preferably less than 225 joules.m$^{-2}$.°C.$^{-1}$.seconds$^{-\frac{1}{2}}$.

According to another object of the invention, there is provided a method of measuring metal purity, comprising: providing a device having a receptacle including a substantially gas-impermeable bottom wall, a hole in said bottom wall and a filter element positioned in said hole, said receptacle being positioned above a collection vessel for collecting molten metal which passes through said filter element from said receptacle and having a leak-tight seal established between said receptacle for molten metal and said collection vessel, and said receptacle being made, at least internally, from an insulating refractory material having a heat diffusivity value sufficiently low that molten metal temperature within said receptacle does not fall below said liquidus temperature during a period in which a vacuum is applied to said collection vessel; introducing a sample of said metal, having a liquidus temperature, in molten form into said receptacle of said device; generating a vacuum within said collection vessel to draw a fixed amount of said molten metal into said collection vessel from said receptacle through said filter; relieving said vacuum when a fixed amount of said metal has been drawn through said filter; and examining said filter to determine a number or type of inclusions deposited on said filter from said fixed amount of metal.

Even when the receptacle for holding the sample of molten metal has low heat diffusivity as indicated, molten metal held in the receptacle for too long tends to freeze because of the thermal mass (heat capacity) of the receptacle. The vacuum should therefore be applied for less time than is required for solidification of the metal, but long enough to withdraw a fixed amount of molten metal through the filter element. In general, unless the receptacle has bee pre-heated, this means that the molten metal should preferably be held for less than five minutes, and more preferably less than two minutes, before the metal sinks in the receptacle to the desired minimum level as a result of being drawn through the filter.

The fixed amount of said metal is preferably drawn through the filter at a rate that exceeds 0.3 kg/minute, more preferably at a rate that exceeds 0.7 kg/minute.

According to yet another aspect of the invention, there is provided a receptacle for filtering a sample of molten metal having a liquidus temperature, said receptacle having a bottom wall provided with a hole, said bottom wall being substantially impermeable to air except at said hole, and a filter element positioned in said hole; wherein said receptacle has a heat diffusivity value that is sufficiently low that, in use, the temperature of molten metal introduced into said receptacle does not fall below said liquidus temperature in a period of time required for an amount of molten metal sufficient for metal purity testing purposes to pass out of said receptacle through said filter element when drawn out by a vacuum created below said filter.

The receptacle may be in the form of a single formed cup of insulating refractory material.

Alternatively, the receptacle may be in a two-part form comprising a cylindrical refractory sleeve open at both ends and having an inner surface and an outer surface, a closing plate of insulating refractory material inserted into the refractory sleeve at a lower end of the sleeve and forming the bottom wall of the receptacle, said closing plate having a circular hole concentrically within the plate, and said closing plate being substantially impermeable to air except at said hole, and a filter element secured within the said circular hole, and a restraining band positioned around the outer surface of the cylindrical refractory sleeve at its lower end to hold the closing plate in place and prevent metal leakage.

The restraining band may, in addition, have a metallic extension which enclosed the exterior of the refractory sleeve over a substantially portion of its length to provide protection to the sleeve during use. The refractory container may alternatively be protected by a separate metallic sleeve placed around the receptacle during use, or mounted as part of the apparatus in which the receptacle is used.

The refractory material at the bottom of the refractory container may itself be impermeable to air or the bottom may be additionally sealed to make it impermeable by the application of a sealing agent such as a glassy material (provided the glassy material is resistance to the molten metal at the temperature of use) to either surface of the refractory material at the bottom of the container.

According to yet another aspect of the invention, there is provided a filter plate for filtering molten metal, comprising a flat insulating refractory plate containing a stepped cylindrical hole positioned within the plate and containing a filter element secured within the stepped hole, said plate having a heat diffusivity value that is less than about 500 joules.m$^{-2}$.°C.$^{-1}$.sec$^{-\frac{1}{2}}$.

The apparatus and method of the present invention are particularly suited for measurement of inclusions in molten aluminum and aluminum alloys, and in particular foundry alloys (for example Al-Si alloys). They are particularly preferred for measurements with aluminum alloys, where the sample temperature is at least 30° C. above the liquidus temperature of the alloy at the time of pouring the sample. In the case of foundry alloys in particular, it has been found that the apparatus and method are effective even very close to the liquidus temperature, and therefore no pre-heating of the receptacle is required. Preheating is not, however, excluded, and simple heating of the interior of the receptacle with a torch, for example, provides adequate heating. Because the receptacle is fabricated from insulating refractory, the heat is retained for long periods of time. Heating may also be carried our merely by pre-contacting the receptacle interior with a sample of the metal, and such heating is sufficiently adequate for all needs.

The insulating refractories used in the receptacle for holding metal are preferably in the form of sintered porous refractories, foamed refractories, or refractories bonded from fibrous refractory materials. These refractories will have either open porosity or closed porosity depending on the manufacturing method and composition. Where refractories with open porosity are used, they generally will have excessive air permeability and must be sealed as described above if used in the bottom of the receptacle. If the refractories have closed porosity, they may have sufficiently low air permeability to be usable without additional sealing. Oxide-based refractory materials are particularly preferred, including oxides of aluminum, silicon, calcium, magnesium and zirconium, and composites of these compounds. The preferred refractory materials will have a thermal conductivity preferably less than about 0.5 watts/m/°C., a density of preferably less than about 1000 Kg/m$^3$, and a specific heat capacity of preferably less than about 1200 joules/Kg/°C., more preferably less than about 1000 joules/Kg/°C. The preferred refractory materials will have a combination of properties such that the heat diffusivity is less than about 500 joules.m$^{-2}$.°C.$^{-1}$.Sec$^{-\frac{1}{2}}$, more preferably less than 350 joules.m$^{-2}$.°C.$^{-1}$.Sec.$^{-1/2}$ and most preferably less than 250 joules.m$^{-2}$.°C.$^{-1}$.Sec$^{-\frac{1}{2}}$. The refractory materials should be resistant to the molten metal and have a service temperature preferably at least 100° C., more preferably at least 200° C. above the liquidus temperature of the metal.

For use in aluminum alloys, a service temperature of 800° C. is generally suitable for the refractory materials. Porous refractory materials based on alumino-silicates (e.g. mullite type material), calcium silicates (e.g. wollastonite type materials) as well as alumina and silica are suitable for this application. Typical materials meeting the requirements for use with aluminum alloys include ISO-400 and B3 refractories supplied by Pyrotek Canada Limited of Drummondville, Quebec. The B3 refractory is a calcium silicate refractory board having thermal conductivity of about 0.2 w/m/°C. and a density of about 850 kg/m$^3$. The board has low permeability to air. The ISO-400 material contains about 80% refractory alumino-silicate fibres (46% alumina, 54% silica), 10 to 20% silica and 4–6% starch binder. It is supplied in prefabricated shapes manufactured by vacuum forming. The density is approximately 370 Kg/m³ and the thermal conductivity is 0.11 to 0.13 w/m/°C. Because of the nature of this material, its air permeability is significant. Both materials have specific heat capacities between about 700 and 800 joules/Kg/°C.

It will be appreciated that the device of the present invention does not require heaters for the receptacle nor pressurizing equipment and enclosures to force the molten metal through the filter. Moreover, by associating a suitable indicator with the molten metal receptacle (e.g. level marks within the interior or an indicator probe attached to the inner sidewall of the receptacle), the need for load measuring devices, etc., can be avoided because the operator can see when a fixed amount of metal has passed from the receptacle through the filter into the collection chamber. Therefore, the device can be made portable, inexpensive and easy to use.

The leak-tight seal provided between the receptacle and the collection chamber is preferably in the form of an elastomeric seal mating with a lower surface of the receptacle or the filter element, most preferably having smooth surfaces. A preferred elastomeric material has an upper service temperature of at least 100° C., most preferably at least 150° C. Elastomeric materials based on fibre reinforced synthetic rubbers, neoprene rubber, Viton™ rubber, etc., may be used in this application.

The vacuum may be applied using a vacuum pump of conventional design, but is more conveniently applied by means of an air aspirator (e.g. a venturi device) which can operate on a plant air supply.

The collection vessel is most conveniently made of metal lined with a refractory material. Refractories of the type used for the refractory container may also be used in this application. It may be constructed of aluminum or steel or any other metal convenient for fabrication, but when used in combination with the lining of refractory material, it must have a surface temperature that in use preferably does not exceed 150° C., more preferably 100° C., and most preferably 50° C., to ensure the integrity of the elastomeric seal.

The metal receptacle preferably has a volume capacity of between about 500 and 2000 cm³.

The filter element preferably has an open area that is generally circular, with a diameter has an open area that is generally circular, with a diameter between about 8 and 20 mm. The permeability of the filter will preferably be between 10 and 30 Darcy, more preferably between 20 and 25 Darcy. It is preferably manufactured from sintered alumina.

The filter element is sealed into the bottom of the receptacle preferably using a refractory cement to prevent leakage around the edges of the filter.

An apparatus of the present type when used with aluminum alloys is operated under conditions such that it filters 1 to 1.5 kg of aluminum alloy in less than 5 minutes and preferably less than 2 minutes. During this time period the heat diffusivity of the receptacle materials is sufficiently low that the alloy temperature does not fall below the liquidus temperature provided the initial temperature of the metal was at least 30° C. above the liquidus temperature.

DETAILED DESCRIPTION OF THE INVENTION

Figure 1:
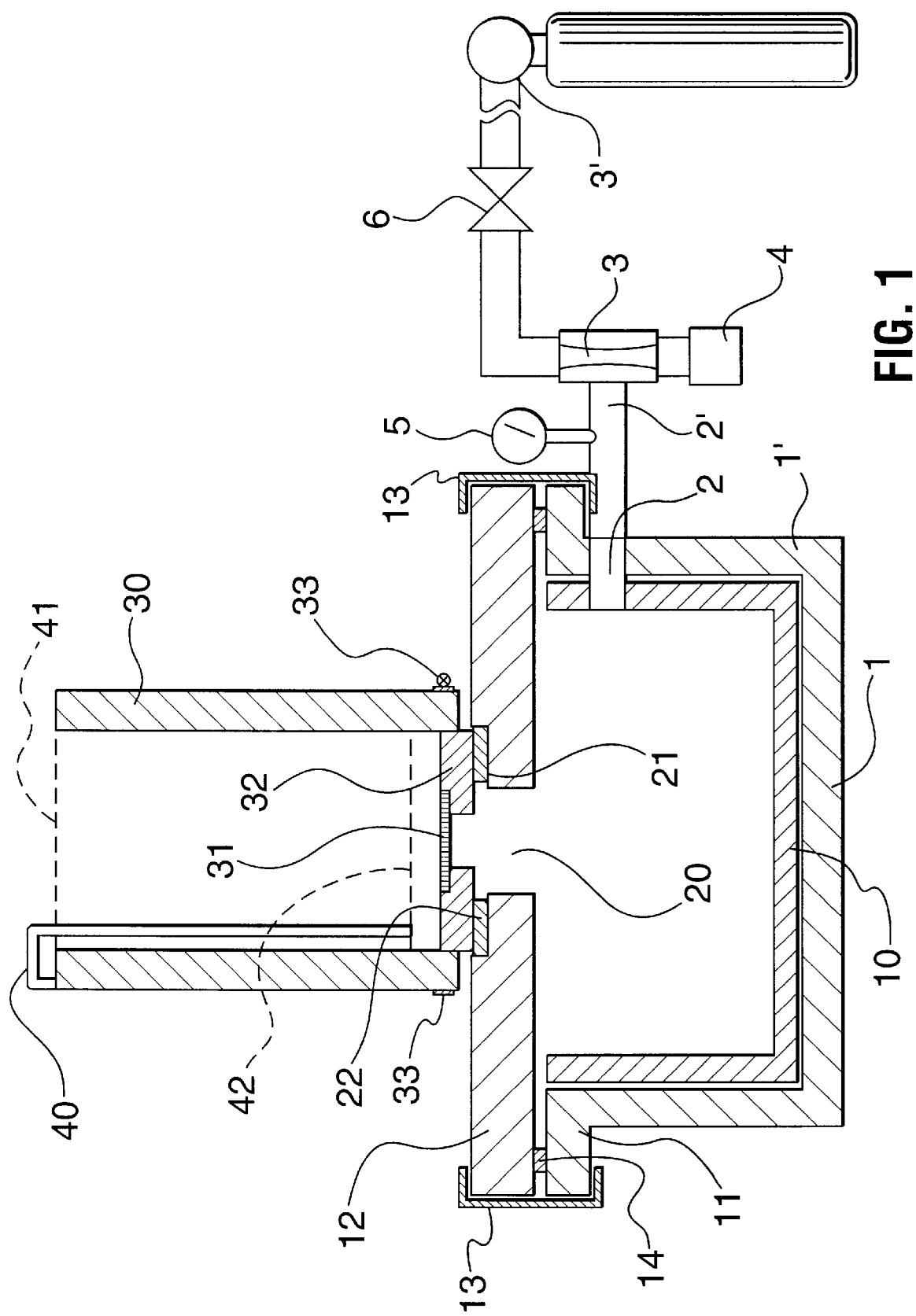
FIG. 1 is a vertical cross-section of a first embodiment of the present invention.

FIG. 1 shows a preferred embodiment of the apparatus of present invention. The apparatus has a generally cylindrical symmetry about a central vertical axis. The apparatus includes a an enclosed collection vessel in the form of a collection chamber 1 constructed of aluminum. In this embodiment, the chamber has a diameter of about 170 mm and weighs about 4 kg. The collection chamber is provided with a passage 2 forming an opening permitting the extraction of gas from the chamber to enable a vacuum to be generated within the chamber. An outer end of the passage 2 is provided with an attachment (not specifically shown) for a gas-conveying tube 2' communicating with a source of vacuum. The source of vacuum includes an air venturi 3 device (Model #20, manufactured by Vac Cubes) which is fed from a source of air 3' typically at 90 psig. The air venturi device has a noise muffler 4 at its downstream end and a vacuum gauge 5 attached to the gas-conveying tube 2' on the collection chamber side of the venturi device. Optionally, a vacuum regulator may be used to control the vacuum in the collection chamber to a fixed value to achieve a relatively constant pressure drop across the apparatus (for example, of between 7 and 12 psig).

The collection chamber 1 comprises two parts, i.e. an open container unit 1' and a top cover 12 provided with a flat lower surface. The top of the container unit 1' in this embodiment has an outwardly-directed flange 11. The top cover in use is held against the flange 11 by means of latching clamps 13. A leak tight elastomeric gasket 14 or an O-ring is provided to create a vacuum seal.

Inside the collection chamber is a refractory liner 10 (fabricated from ISO-400 fibrous insulating refractory—provided by Pyrotek Canada Limited of Drummondville, Quebec, Canada) to protect the walls of the collection chamber. The liner 10 is approximately 12 mm in thickness, with an internal diameter of 140 mm and a depth of 137 mm. The refractory liner 10 ensures that the walls of the collection chamber remain cool through repeated operations and permits relatively low temperature materials to be used for gaskets and seals, i.e. the insulation at least partially shields the gasket 14 from the high temperature of the molten metal held within the chamber.

The top cover 12 has a centrally located hole 20 of 25 mm in diameter and a seat 21 of 79 mm in diameter and 6.3 mm in depth in which is placed a ring 22 of elastomeric material, with a central hole 23 of approximately the same size as the hole 20 in the top cover. The elastomeric material is typically GARLOCK™ rubber (a fibre reinforced synthetic rubber manufactured by Garlock Inc. of Newtown, Pa.) cut from material approximately 0.8 to 3.7 mm thick. The thickness of the elastomeric ring 22 is slightly less than the depth of the seat 21.

A refractory crucible 30 provides a receptacle for a sample of molten metal to be tested. The crucible is formed from a cylindrical tube of fibrous refractory material (for example ISO-400 manufactured by Pyrotek Canada Limited), 100 mm in outer diameter (OD), 75 mm in inner diameter (ID), and 150 mm in length, forming a side wall of the crucible, and a circular refractory plate 32 forming a bottom wall having a central hole 13 mm in diameter. A filter element 31 (supplied by Bomem Inc. of Quebec, Quebec, Canada) 25 mm in diameter and 3.5 mm thick is glued using FIBERFAX™ QF150 cement into a seat machined into said circular refractory plate 32 around the central hole. The plate is fabricated from B3 refractory board, supplied by Pyrotek. The plate 32 is fitted into one end of the refractory tube with a small portion (5 to 15 mm) projecting below the lower end of the tube, and is held in place with a large hose clamp 33. The completed crucible sits on top of the elastomeric ring 22 in the seat 21. By this means, a leak-tight seal is established between the crucible 30 and the collection chamber 1. The elastomeric ring is insulated from the high temperature of the molten metal by the refractory plate 32. The cover 12 on the lower side of the elastomeric ring does not usually get very hot because it does not contact molten metal for a very long period time, if at all.

In use, the refractory crucible 30 is filled with molten metal to a top level 41. An indicator pointer 40 is fixed in place. Air pressure is applied to the venturi device 3 by opening valve 6 and the metal level is observed in the refractory crucible. When the level reaches the lower end of the pointer 40 at level 42, the valve 6 is closed and the vacuum broken to stop the metal flow. The residual metal is allowed to freeze in the refractory crucible 30 and the filter 31. On disassembly, the still-molten metal in the collection chamber 1 can be emptied, and the equipment re-assembled with a new refractory crucible-filter combination 30, 31 for immediate re-use.

It should be noted that it would be undesirable to draw all of the molten metal through the filter 31 as this would detrimentally affect the nature of the material observed on the filter, and hence the analysis. It is therefore preferred to leave a small amount of metal remaining in the receptacle (e.g. 6 to 10 mm) so that the filter does not become uncovered or "run dry." In the present apparatus, the desired lower level is easily detected in use, so larger amounts of metal do not have to be allowed to remain in order to prevent "overshoot", as is the case with some known devices.

The refractory crucible 30 containing the frozen sample is readily disassembled and a replacement base 32 and filter 31 inserted ready for re-use. The filter 31 and associated metal also is readily separated from the base 32 and is of a convenient size for sectioning and analysing for inclusion counts and type. Because the metal level in the refractory crucible can be readily observed (unlike devices requiring pressurizing hoods), smaller amounts of residual metal need be left in the apparatus, which makes sectioning and analysis easier.

The use of insulating refractory elements 10, 30, 32 means that elastomeric materials having relatively low upper temperature limits can be used, since elastomeric materials are positioned on the cool side of the insulation. Elastomeric materials permit good vacuum seals to be attained without clamps or other holding methods normally required with high temperature seals, and thereby permits the use of lighter materials of construction throughout.

Figure 2:
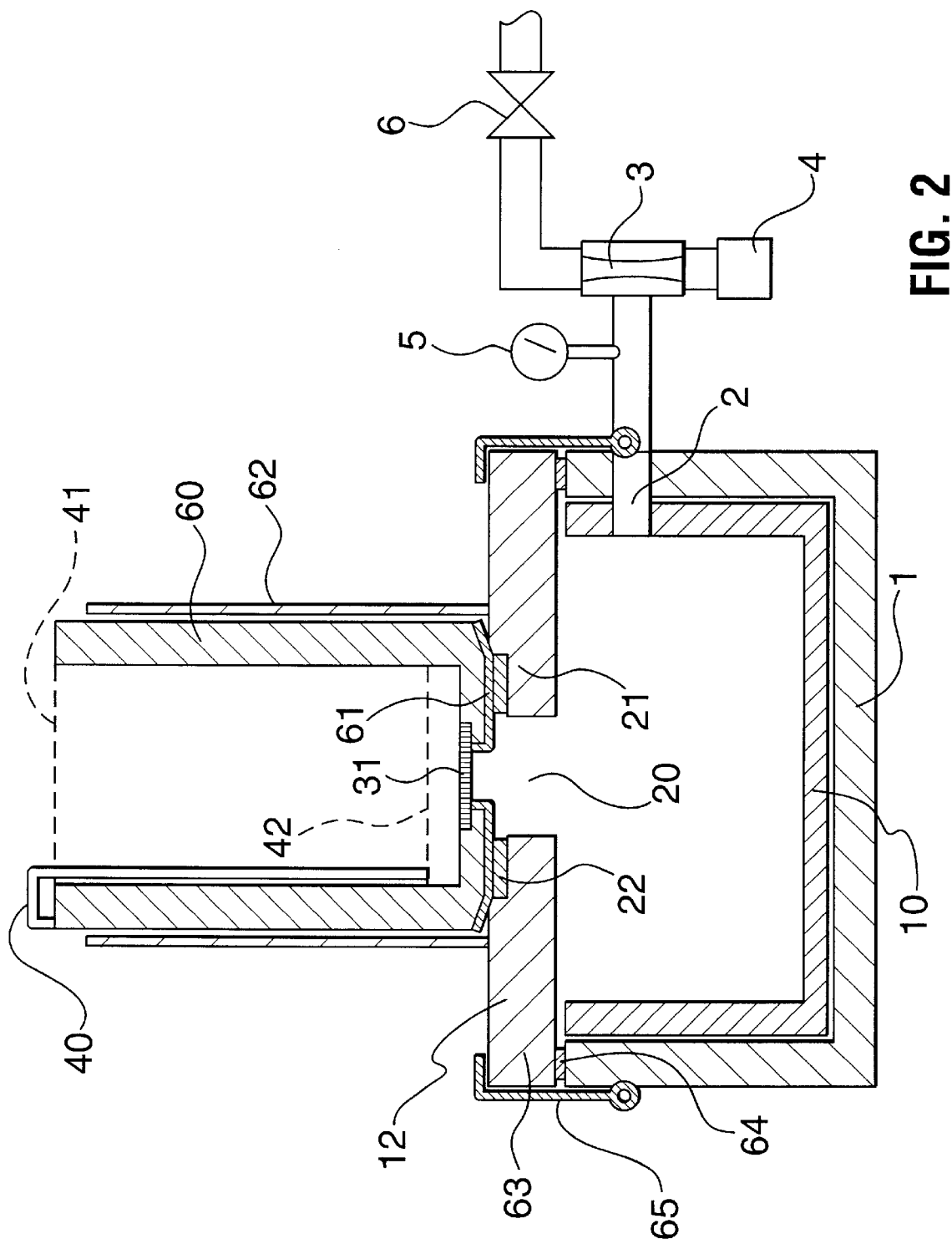
FIG. 2 is a vertical cross-section of a second embodiment of the present invention.

A second embodiment of the present invention is illustrated in FIG. 2. In this embodiment, the receptacle 60 for the metal is in the form of a one-piece cup with sidewalls and a bottom. The bottom contains the filter element 31 mounted as in FIG. 1. The cup is fabricated from ISO-400 refractory material and the bottom face 61 of the cup is sealed using a glassy material having an upper service temperature of at least 700° C. This sealing layer may be formed by fusing the surface of the refractory material by locally applied heat, or by impregnating the surface with powdered glass (for example Pyrex™ glass) and fusing. Also provided in this embodiment is a shield 62 welded to the top of the cover 63, and surrounding the receptacle for much of its height. This protects the receptacle from damage during use, the protects the operator in case of failure of the receptacle.

The collecting vessel in this embodiment has no flange at the upper surface, but the top of the collection vessel wall is machined so that an elastomeric seal 64 may be placed between it and the cover. Latching clamps 65 are provided, and may be attached to the sides of the collection vessel, for example, by hinges.

Although the present invention has been explained above with reference to specific embodiments, it will be appreciated by persons skilled in the art that modifications and variations of those embodiments may be made without departing from the scope of the invention as defined by the following claims.

What we claim is:

1. A device for measuring metal purity, comprising:
   a receptacle for holding a sample of molten metal at a temperature above a liquidus temperature of said metal, said receptacle being made, at least internally, from an insulating refractory material having a heat diffusivity value, said receptacle having a bottom wall provided with a hole, and said bottom wall being substantially impermeable to air except at said hole;
   a filter element for collecting impurities from said molten metal, said filter element being positioned in said hole; and
   an enclosed collection vessel positioned below and separable from said receptacle for collecting molten metal which passes through the filter element from said receptacle, said collection vessel having an opening permitting extraction of gas from within said vessel to enable a vacuum to be generated within said vessel during use of the device;
   wherein a leak-tight seal is established between a bottom of said receptacle for molten metal and said collection vessel to permit vacuum generated in said collection vessel to draw molten metal into said collection vessel from said receptacle through said filter; and
   wherein said heat diffusivity value of said insulating refractory material of said receptacle is sufficiently low that, in use, the temperature of the molten metal in said receptacle does not fall below the liquidus temperature in the absence of further addition of heat in a period of time after introduction of the metal into the receptacle required for said vacuum to draw a fixed amount of said molten metal sufficient for metal purity testing purposes from said receptacle through said filter and into said collection vessel.

2. The device of claim 1, wherein said heat diffusivity value is less than about 500 joules.m.$^{-2}$.°C.$^{-1}$ sec$^{-\frac{1}{2}}$.

3. The device of claim 1, wherein said heat diffusivity value is less than about 350 joules.m.$^{-2}$.°C.$^{-1}$.sec$^{-\frac{1}{2}}$.

4. The device of claim 1, wherein said heat diffusivity value is less than about 225 joules.m.$^{-2}$.°C.$^{-1}$.sec$^{-\frac{1}{2}}$.

5. The device of claim 1, wherein said insulating refractory material of said receptacle is a porous insulating refractory sealed against air-permeability at said bottom wall.

6. The device of claim 1, wherein said insulating refractory material of said receptacle is resistant to said molten metal and has a service temperature at least 100° C. above the liquidus temperature of the metal.

7. The device of claim 1, wherein said hole and said filter are sized such that said fixed amount of molten metal may be drawn into said collection chamber in about 5 minutes or less.

8. The device of claim 1, wherein said hole and said filter are sized such that said fixed amount of molten metal may be drawn into said collection chamber in about 2 minutes or less.

9. The device of claim 1, wherein said receptacle contains an indicator to indicate when a measured amount of said molten metal has passed through said filter into said collection chamber.

10. The device of claim 1, wherein said receptacle for said molten metal has a side wall, and wherein said bottom wall of the receptacle holding said filter is detachable from said side wall. inclusions deposited on said filter from said fixed amount of metal.

11. The device of claim 1, wherein said insulating refractory is an oxide-based refractory material selected from the group consisting of oxides of aluminum, silicon, calcium, magnesium and zirconium, and composites of said oxides.

12. The device of claim 11, wherein said insulating refractory is selected from the group consisting of sintered porous refractories, foamed refractories, and refractories bonded from fibrous refractory materials.

13. The device of claim 1, wherein said collection vessel is made of, or internally lined with, an insulating refractory material.

14. The device of claim 13, wherein said collection vessel comprises an open container unit and a top cover for closing said unit, and wherein a leak-tight elastomeric seal is provided between said open container unit and said cover, said seal being provided at a position where it is at least partially shielded from molten metal temperatures by said insulating refractory material.

15. The device of claim 1, wherein said leak-tight seal between said receptacle and said collection chamber comprises an elastomeric seal element positioned between said bottom wall of said receptacle and said collection chamber and surrounding said hole and said filter.

16. The device of claim 15, wherein said elastomeric seal element has an upper service temperature of at least 100° C.

17. The device of claim 1, wherein said collection vessel has a side wall, and wherein said opening for vacuum generation is a passage provided in said side wall at an upper region thereof, an outer end of said passage being provided with an attachment for a gas-conveying tube.

18. The device of claim 17, including a vacuum generator comprising an air venturi device provided with a gas-withdrawing orifice, said gas-withdrawing orifice being connected to said gas-conveying tube.

19. A method of measuring metal purity, comprising:
providing a device having a receptacle including a substantially gas-impermeable bottom wall, a hole in said bottom wall and a filter element positioned in said hole, said receptacle being separably attached to and positioned above a collection vessel for collecting molten metal which passes through said filter element from said receptacle and having a leak-tight seal established between a bottom of said receptacle for molten metal and said collection vessel, and said receptacle being made, at least internally, from an insulating refractory material having a heat diffusivity value sufficiently low that molten metal temperature within said receptacle does not fall below said liquidus temperature in the absence of further addition of heat during a period of time after the introduction of metal into the receptacle in which a vacuum is applied to said collection vessel to draw a fixed amount of metal into the receptacle;
introducing a sample of said metal, having a liquidus temperature, in molten form into said receptacle of said device;
generating a vacuum within said collection vessel to draw said fixed amount of said molten metal into said collection vessel from said receptacle through said filter;
relieving said vacuum when said fixed amount of said metal has been drawn through said filter; and
examining said filter to determine a number or type of inclusions deposited on said filter from said fixed amount of metal.

20. The method of claim 19, wherein said heat diffusivity value of said refractory material of said receptacle is less than about 500 joules.m$^{-2}$.°C.$^{-1}$.sec$^{-\frac{1}{2}}$.

21. The method of claim 19, wherein said fixed amount of said molten metal is drawn into said collection chamber in a period of about 5 minutes or less.

22. The method of claim 19, wherein said fixed amount of said molten metal is drawn into said collection chamber in a period of about 2 minutes or less.

23. The method of claim 19, wherein said vacuum is generated within said collection chamber by passing a gas through a venturi vacuum device communicating with an interior of said collection vessel.

24. A receptacle for filtering a sample of molten metal having a liquidus temperature, said receptacle having a bottom wall provided with a hole, said bottom wall being substantially impermeable to air except at said hole, and a filter element intended for vacuum filtration positioned in said hole; wherein said receptacle has a heat diffusivity value that is sufficiently low that, in use, subject to the application of a vacuum to an underside of said filter, the temperature of molten metal introduced into said receptacle does not fall below said liquidus temperature in the absence of further addition of heat in a period of time after introduction of metal into the receptacle required for an amount of molten metal sufficient for metal purity testing purposes to pass out of said receptacle through said filter element when drawn out by said vacuum created below said filter.

25. The receptacle of claim 24, wherein said heat diffusivity value is less than about 500 joules.m$^{-2}$.°C.$^{-1}$.sec$^{-\frac{1}{2}}$.

26. The receptacle of claim 24, wherein said heat diffusivity value is less than about 350 joules.m$^{-2}$.°C.$^{-1}$.sec$^{-\frac{1}{2}}$.

27. The receptacle of claim 24, wherein said heat diffusivity value is less than about 225 joules.m$^{-2}$.°C.$^{-1}$.sec$^{-\frac{1}{2}}$.

28. The receptacle of claim 24, wherein said insulating refractory is an oxide-based refractory material selected from the group consisting of oxides of aluminum, silicon, calcium, magnesium and zirconium, and composites of said oxides.

29. The receptacle of claim 28, wherein said insulating refractory is selected from the group consisting of sintered porous refractories, foamed refractories, and refractories bonded from fibrous refractory materials.

30. The receptacle of claim 24, wherein said insulating refractory material of said receptacle is a porous insulating refractory sealed against air-permeability at said bottom wall.

31. The receptacle of claim 24, wherein said insulating refractory material of said receptacle is resistant to said molten metal and have a service temperature at least 100° C. above the liquidus temperature of the metal.

32. The receptacle of claim 24, wherein said hole and said filter element are sized such that said sufficient amount of molten metal may be drawn through said filter element in about 5 minutes or less.

33. The receptacle of claim 24, wherein said hole and said filter are sized such that said sufficient amount of molten metal may be drawn through said filter element in about 2 minutes or less.

34. The receptacle of claim 24, including a side wall, and wherein said bottom wall of the receptacle holding said filter is detachable from said side wall.

35. A device for measuring metal purity, comprising:
a receptacle for holding a sample of molten metal having a liquidus temperature, said receptacle being made, at least internally, from an insulating refractory material having a heat diffusivity value, said receptacle having a bottom wall provided with a hole, and said bottom wall being substantially impermeable to air except at said hole;

a filter element for collecting impurities from said molten metal, said filter element being positioned in said hole; and an enclosed collection vessel made of, or internally lined with, an insulating refractory, positioned below said receptacle for collecting molten metal which passes through the filter element from said receptacle, said collection vessel having an opening permitting extraction of gas from within said vessel to enable a vacuum to be generated within said vessel during use of the device, and said collection vessel comprising an open container unit and a top cover for closing said unit, and wherein a leak-tight elastomeric seal is provided between said open container unit and said cover, said seal being provided at a position where it is at least partially shielded from molten metal temperatures by said insulating refractory material;

wherein a leak-tight seal is established between said receptacle for molten metal and said collection vessel to permit vacuum generated in said collection vessel to draw molten metal into said collection vessel from said receptacle through said filter;

wherein said heat diffusivity value is sufficiently low that, in use, the temperature of the molten metal in said receptacle does not fall below the liquidus temperature in a period of time required for said vacuum to draw a fixed amount of said molten metal sufficient for metal purity testing purposes from said receptacle through said filter and into said collection vessel; and wherein said open container unit of said collection vessel has a side wall provided with an outwardly-projecting flange at an upper end thereof, and wherein said elastomeric seal is positioned between said upper cover and said flange.

36. A receptacle for filtering a sample of molten metal having a liquidus temperature, said receptacle having a bottom wall provided with a hole, said bottom wall being substantially impermeable to air except at said hole, and a filter element positioned in said hole; wherein said receptacle has a heat diffusivity value that is sufficiently low that, in use, the temperature of molten metal introduced into said receptacle does not fall below said liquidus temperature in a period of time required for an amount of molten metal sufficient for metal purity testing purposes to pass out of said receptacle through said filter element when drawn out by a vacuum created below said filter; said receptacle comprising a cylindrical refractory sleeve open at both ends and having an inner surface and an outer surface, a closing plate of insulating refractory material inserted into the refractory sleeve at a lower end of the sleeve, said closing plate having a circular hole concentrically within the plate, and said closing plate being substantially impermeable to air except at said hole, a filter element secured within the said circular hole, and a restraining band positioned around the outer surface of the cylindrical refractory sleeve at its lower end to hold the closing plate in place and prevent metal leakage.

* * * * *